United States Patent
Muskulus et al.

(10) Patent No.: US 7,732,474 B2
(45) Date of Patent: Jun. 8, 2010

(54) PHARMACEUTICAL PREPARATION CONTAINING A BENZIMIDAZOLE COMPOUND MIXED WITH MICROCRYSTALLINE CELLULOSE AND A METHOD FOR ITS PREPARATION

(75) Inventors: Frank Muskulus, Gröbenzell (DE); Peter Kraaβ, München (DE); Andrea Burgenmeister, Merklingen (DE)

(73) Assignee: Ratiopharm, GmbH, Ulm (DE)

( * ) Notice: Subject to any disclaimer, the term of this patent is extended or adjusted under 35 U.S.C. 154(b) by 1423 days.

(21) Appl. No.: 10/522,784

(22) PCT Filed: Jul. 16, 2003

(86) PCT No.: PCT/EP03/07741

§ 371 (c)(1),
(2), (4) Date: Feb. 24, 2005

(87) PCT Pub. No.: WO2004/014345

PCT Pub. Date: Feb. 19, 2004

(65) Prior Publication Data

US 2005/0129760 A1 Jun. 16, 2005

(30) Foreign Application Priority Data

Aug. 2, 2002 (DE) ................................ 102 35 475

(51) Int. Cl.
*A61K 31/4184* (2006.01)
*A61K 9/24* (2006.01)
*A61K 47/38* (2006.01)

(52) U.S. Cl. ........................ 514/394; 424/472; 514/781; 514/970

(58) Field of Classification Search ....................... None
See application file for complete search history.

(56) References Cited

U.S. PATENT DOCUMENTS 5,824,339 A * 10/1998 Shimizu et al. ............. 424/466
6,096,340 A 8/2000 Chen et al.

FOREIGN PATENT DOCUMENTS

| DE | 196 26 045 | 1/1998 |
|---|---|---|
| EP | 1 010 423 | 6/2000 |
| EP | 1 108 425 | 6/2001 |
| WO | WO01/52816 | 7/2001 |

OTHER PUBLICATIONS

International Search Report for PCT Application No. PCT/EP03/07741.
Examination Report for German Application No. 102 35 475.8.

* cited by examiner

*Primary Examiner*—Johann R Richter
*Assistant Examiner*—Frank I Choi
(74) *Attorney, Agent, or Firm*—Dobe Law Group, LLC; Christopher Aniedobe

(57) ABSTRACT

The present invention relates to oral pharmaceutical preparations in the form of pellets in which a benzimidazole compound is stabilized by combining it with microcrystalline cellulose.

19 Claims, No Drawings

PHARMACEUTICAL PREPARATION CONTAINING A BENZIMIDAZOLE COMPOUND MIXED WITH MICROCRYSTALLINE CELLULOSE AND A METHOD FOR ITS PREPARATION

The present invention relates to a new galenic formulation of a benzimidazole compound, in particular of omeprazole, but also lansoprazole, rabeprazole or pantoprazole, that has excellent storage stability. Stability is achieved by combining the benzimidazole compound in mixture with microcrystalline cellulose in the form of a layer containing an active ingredient on an inert core (a neutral pellet). The invention also relates to a method for preparing a formulation of the aforementioned kind and the use of microcrystalline cellulose for stabilizing a benzimidazole compound of this type.

Benzimnidazole compounds of formula I

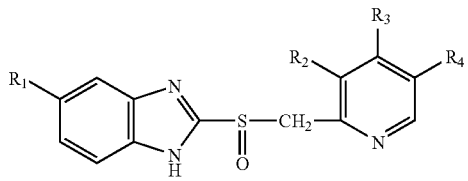

in which R1 is hydrogen, methoxy or difluoromethoxy, R2 is hydrogen, methyl or methoxy, R3 is methoxy, 2,2,2-trifluoroethoxy or 3-methoxypropoxy and R4 is hydrogen methyl or methoxy, are well known and very effective medicinal substances widely used in the treatment of gastric disorders. Among these compounds in particular are omeprazole, lansoprazole, rabeprazole and pantoprazole. However, benzimidazole compounds of formula 1 tend to disintegrate and it is difficult to provide sufficiently stable pharmaceutical preparations that contain these compounds.

Thus, benzimidazole compounds of formula I, in particular omeprazole, are labile in an acidic aqueous solution, and for that reason benzimidazole compounds were first combined in galenic formulations with an alkaline buffer. An example of a formulation of this type is described in European patent publication EP-A 0 247 983.

Combining benzimidazole compounds with an alkaline buffer can produce galenic formulations that have a very high degree of stability. There are, however, problems inherent to such galenic formulations; for example, acid groups present in the enteric coating of the formulations can react with the alkaline-reacting compound of the core. Though it is well known to separate the alkaline-reacting core from the enteric coating by means of a separating layer, great care must be taken in the preparation of galenic formulations of this type to adjust the thickness and type of separating layer and the type of enteric coating to the alkalinity of the core in order to obtain a galenic formulation with sufficiently high degree of stability and bio-availability. These problems are discussed, for example, in Example 1 of European patent publication EP-A 0 247 983.

In the meantime formulations have also been developed in which the benzinidazole compound is not combined with an alkaline buffer. An example of this type of formulation is described in U.S. Pat. No. 5,626,875, corresponding to European patent publication EP-A 0773 025. This publication discloses a formulation comprising an inert core coated with a first layer that contains the Benzimnidazole compound together with a water soluble polymer, in addition to a second layer containing a water soluble polymer and a third layer consisting of an enteric coating. The pharmaceutical preparations described in concrete terms above all contain a benzimidazole compound mixed with talc.

In addition, omeprazole-containing pharmaceutical preparations have also been developed in which omeprazole is combined with a specific stabilizer for enhancing the stability of the omeprazole. Known stabilizers are, for example, mannitol (EP-A 0 646 006), $TiO_2$ (WO 96/37195) or cyclodextrine, (WO 98/40069), as well as amino acids.

Finally, German patent publication DE-A 199 59 419 (corresponding to WO 01/41734) discloses stabilizing benzimidazole compounds of formula 1 by combining them with a compound that provides a specific pH-value below pH 7, preferably with sodium dihydrogen phosphate ($NaH_2PO_4$). The pharmaceuticals disclosed in DE-A 199 59 419 exhibit a high degree of stability, but such pharmaceuticals are somewhat difficult and laborious to produce, since the pH range within which optimum stability is achieved is relatively narrow, and the starting materials used in the preparation of such formulations must be carefully and constantly monitored in order to ensure the desired pH-range.

Thus, there still exists the need for galenic formulations for benzimidazole compounds of formula I that have excellent stability. Such formulations should be minimal in structure and should not be stabilized by means of adjustment to a specific pH-value. The expedients used for such formulations should be those known in the galenic prior art. Finally, formulations of this type should have at least as much stability as those pharmaceuticals already marketed, and preferably greater stability.

It was unexpectedly found that microcrystalline cellulose is capable of stabilizing Benzimnidazole compounds of formula 1, in particular omeprazole, pantoprazole, rabeprazole and lansoprazole. Microcrystalline cellulose is known for a variety of pharmaceutical applications, in particular as a filler and binding agent, in granulation, for direct tabletting, as an enhancer of tablet decomposition and as a filler used in the production of capsules, but it is unconventional to use it in the manufacture of pellets made by a coating process, such as for example, powder-coating or suspension coating, that is pellets having an inert core to which coated layers are applied (e.g. from solution or dispersion).

When used in accordance with the present invention for stabilizing a Benzimnidazole compound of formula 1 in a layer of a pellet containing the active ingredient, it is especially advantageous if the microcrystalline cellulose particles are as small as possible in size, and it is presumed that stabilization occurs through interaction with the extensive surfaces of the microcrystalline cellulose. Thus, according to the present invention microcrystalline cellulose with minimum particle size is especially preferred. Further, the distribution of particle size should such as to minimize the number of large particles.

Unless otherwise apparent herein, the microcrystalline cellulose herein refers to the type that meets the standards set forth in the U.S. Pharmacopeia and/or the European pharmacopeia and/or the German pharmacopeia or their corresponding monographs.

There are various methods for measuring the size of particles or determining the distribution of particle size of the microcrystalline cellulose such as for example, the technique of light scattering as employed by devices of Malvern Instruments, e.g. the "Malvern MasterSizer X", mechanical sieve shakers, as used by FMC for determining the distribution of granular size of its AVICEL PH®-products, or also "air-jet"

sieve analyses, which can be performed, for example, with an ALPINA®-"air jet" model 200.

Unless otherwise indicated or apparent herein, the data on mean particle size or distribution of particle size refer within the scope of the specification to values that were obtained using a mechanical sieve shaker. To this end a 100 g sample was sifted for a period of 20 minutes in a mechanical sieve shaker fitted with suitably sized sieve openings. This method corresponds to the determination of mean particle size and/or distribution of particle size, as indicated for AVICEL PH®-products in the product specifications, and e.g. for AVICEL PH®-products described in the literature, e.g. in Fiedler, Lexikon der Hilfstoffe für Pharmazie, Kosmetik angrenzende Gebiete, 5$^{th}$ ed., 2002. (Fiedler's Encyclopedia of Excipients Used in Pharmaceutical Cosmetic and Related Fields).

Insofar as a determination in this manner is technically unfeasible with respect to a given product, a determination is made, unless otherwise indicated herein, by means of a so-called "air jet"-sieve analysis, for example, on an ALPINA®-"air jet"-sieve, model 200 at a reduced pressure of approximately 10 to 12 inches of water. For a 60-mesh sieve 100 g are treated for 3 minutes, for a 100-mesh sieve 50 g are also treated for 3 minutes, for a 200-mesh sieve 50 g are treated for 6 minutes, and for a 400-mesh sieve 20 g are treated for 3 minutes.

To the extent that particle size distribution is defined in this application by the data relative to $d_{10}$-, $d_{50}$-, and $d_{90}$-values, the $d_{10}$-value signifies that 10% of the particles are smaller than the given $d_{10}$-value, unless otherwise indicated herein (a corresponding definition is valid for the $d_{50}$- and $d_{90}$-values).

Instead of using precise data on particle size distribution, a definition of the preferred microcrystalline cellulose can also be made for the purposes of the present invention from data on bulk density. Unless otherwise indicated herein, bulk density is determined as follows: A container with an inner diameter of 30.0±2.0 mm and a calibrated volume of 25.0±0.5 ml is weighed and placed beneath a volume measurement device fitted with a 10-mesh screen. The powder is poured slowly from a height of 2" above the funnel through the volume measurement device at a rate that inhibits clumping until the container overflows. The excess powder is removed (being careful not to compact the powder and that no additional powder drops into the container), after which the filled container is weighed. The bulk density is determined by dividing the weight of the powder within the container by the container volume. If required for technical reasons, the 10-mesh screen may be removed in the case of extremely fine-grained powder. Reference is also made to the provisions under DIN-ISO 697: 1984-01 (German Industrial Standards).

When defining microcrystalline cellulose from data on mean particle size and distribution of particle size, preferred microcrystalline cellulose according to the present invention has a mean particle size of 100 µm or less, and it is also preferable if microcrystalline cellulose of the aforementioned kind has a granular size distribution (particle size distribution) in which less than 10% of the particles are 250 µm or greater in size and less than 50% of the particles are 75 µm or greater in size. Even more preferred is microcrystalline cellulose with a mean particle size of 50 µm or less, and preferably microcrystalline cellulose of this kind has a particle size distribution in which less than 2% of the particles are 250 µm or greater in size and less than 30% of the particles are 75 µm or greater in size. Still more preferred is microcrystalline cellulose with a mean particle size of e.g. about 30, about 25, about 20, about 15 or about 10 µm. Particle size distribution for such microcrystalline cellulose should be as narrow as possible, and preferably less than 0.1% of the particles are 250 µm or greater in size and less than 1% of the particles are 75 µm or greater in size.

When determining the particle size distribution of microcrystalline cellulose using a light scattering technique, the microcrystalline celluloses preferably used are summarized in the following table (in which determination was made using a MasterSizer of Malvern Instruments):

| Preferred mean particle size | preferred particle size distribution Determined using Malvern MasterSizer | | |
|---|---|---|---|
| | $d_{10}$ | $d_{50}$ | $d_{90}$ |
| 90 µm or less | 25-46 µm | 98-146 µm | 195-276 µm or narrower |
| 50 µm or less | 16-25 µm | 46-76 µm | 92-165 µm or narrower |
| about 15 µm | >6 µm | 12-18 µm | >70 µm or narrower |

When defining microcrystalline cellulose based on bulk density, it is preferable to have microcrystalline cellulose with a bulk density of 0.30 g/cm$^3$ or less, even more preferable is microcrystalline cellulose with a bulk density of 0.29 g/cm$^3$ or less, still more preferable is microcrystalline cellulose with a bulk density of 0.28 g/cm$^3$ or less and most preferable is microcrystalline cellulose with a bulk density of 0.27 g/cm$^3$ or less.

The microcrystalline cellulose used should be as finely grained as possible, but it may also be advantageous for processing reasons to use microcrystalline cellulose with a mean particle size of e.g. 1 µm or greater, for example, 5 µm or greater. It may be equally advantageous to use microcrystalline cellulose with a powder density of 0.109 g/cm$^3$ or greater, for example, of 0.15 g/cm$^3$ or more, for example 0.20 g/cm$^3$ or greater.

According to the present invention, it is preferable to use microcrystalline celluloses that are commercially available. Suitable products are the microcrystalline celluloses in the AVICEL PH®-series from FMC which, e.g. are described in detail in Fiedler's Encyclopedia of Excipients Used in the Pharmaceutical, Cosmetic and Related Fields, 5$^{th}$ ed., 2002, products in the EMCOCEL-series of Mendell, microcrystalline cellulose in the ELCEMA-series of Degussa AG, microcrystalline cellulose in the SANACEL-series of Cerestar Deutschland, microcrystalline cellulose in the SOLKA-FLOC-series of Paul Brem and the microcrystalline cellulose in the VIVAPUR-series of Rettenmeier & Sons. The most preferred products are those from the AVICEL PH® series of FMC. With regard to product specifications and in particular particle size and particle size distributions of the aforementioned preferred microcrystalline celluloses, reference is made in particular to the aforementioned Fiedler Encyclopedia and also to known and published product specifications of the manufacturers.

The pharmaceutical preparations according to the present invention consist of pellets with an inert core to which a layer containing an active ingredient is applied. Applied to said layer with active ingredient are preferably one or more inert layers (separating layers). Further, the pellet has an outer layer comprising an enteric coat, that is, an enteric layer.

The inert core is preferably a known sugar/starch-core. Cores of this type are commercially available.

The layer with the active substance applied to the core contains the active ingredient, the benzimidazole compound and the microcrystalline cellulose in addition to other optional, pharmaceutically compatible excipients. Generally, the layer with the active ingredient also contains a binder. The separating layer preferably also contains microcrystalline cellulose and will generally also contain a binder. Additional conventional excipients may also be present. The enteric coating serves as a classic enteric layer. It comprises common enteric substances known from the prior art, such as cellulose ester and methacrylic acid-type copolymers, e.g. methacrylic acid/(meth)acrylic acid alkylester copolymers, sold for example under the marks Eudragit®L or Eudragit®S.

Triethylcitrate, dibutylphthalate, propylenglycol, and/or polyethylenglycol or similar compounds may preferably be used as a plasticizer in the enteric coating. The enteric coating may also contain other conventional excipients.

The binder present in the layer with the active ingredient and in the optional separating layers is preferably a water-soluble polymer or a polymer that rapidly decomposes in water. It is preferable to use the same water-soluble polymer in both the layer with the active ingredient, as well as in all separating layers in which a binder is present; however, it is also feasible to use different water-soluble polymers or polymers that rapidly decompose in water in the various layers. According to the present invention it is especially preferable to use hydroxypropylmethylcellulose and hydroxypropylcellulose as binder.

Conventional, pharmaceutically compatible excipients known to those skilled in the art may be present in each of the layers of the pharmaceutical preparation. Those skilled in the art may easily determine type and quantity of such excipients based on their general knowledge of the field. Unless otherwise indicated the excipients comprise conventional binders, plasticizers, dyes, pigments, such as titanium dioxide, talc and other known excipients.

In general the pellets are filled in a conventional gelatin capsule or compressed into so-called "multiple unit tablets". When compressing into "multiple unit tablets" the enteric layer must be formed so that it is not destroyed during compression, and the storability of the tablets is not compromised. The manner in which the enteric layer must be formed to enable compression into a "multiple unit tablet" is known to those skilled in the art, e.g. from European patent publication EP-A 723 436 or from the publication "Drugs made in Germany, No. 2 1994, pages 53 et seq.

The amount of active ingredient in the layer of the pellet containing said active ingredient is set such that the desired dosage can be given by administering it in a unit dosage form, such as a gelatine capsule or a "multiple unit tablet". Unit dosages typically used for omeprazole, for example, are 10 mg, 20 mg or 40 mg per capsule. However, other dosages are equally feasible. Generally the amount of active ingredient is selected so that in each pellet the layer with said active ingredient (depending on size of pellet and desired unit dosage) contains from 0.001 to 10 mg, preferably from 0.01 to 1 mg, in particular from 0.05 to 0.5 mg of the benzimidazole compound of formula I.

The amount of microcrystalline cellulose in the layer containing the active ingredient is variable across a broad range. Preferably, the amount of microcrystalline cellulose, in the layer with said active ingredient, is 10 to 150%, more preferably, 25 to 150%, in particular 50 to 150% by weight based the amount of active ingredient. It is most preferable if the amount of microcrystalline cellulose is approximately the same as or less than the amount of active ingredient in the layer containing said active ingredient, for example, about 50% of the amount of active ingredient in said layer containing the active ingredient.

The amount of binder in the layer with the active ingredient is not particularly limited and is easily ascertained by one skilled in the art. Based on the amount of active ingredient in said layer containing the active ingredient, the amount of binder is preferably 25% to 150% by weight, more preferably 50% to 125% by weight, and it is most preferred if the amount of binder is substantially the same as, or is less than, the amount of active ingredient in said layer containing the active ingredient.

Preferably, the pharmaceutical preparation according to the present invention has at least one separating layer disposed between the layer containing the active ingredient and the enteric coating, especially preferred is a single separating layer. Generally, the separating layer also contains a binder, preferably the same binder that is used in the layer containing the active ingredient. Other conventional binders as specified above may also be used, however. Preferably, the separating layer or layers also contain microcrystalline cellulose, as specified above. The amount of microcrystalline cellulose is not strictly limited, though preferably the amount of microcrystalline cellulose in the separating layer is about 25 to 100%, based on the weight of the binder. The separating layer may also contain other conventional excipients.

The pharmaceutical preparation according to the present invention is manufactured according to known methods. The coating steps are preferably performed in a fluidized bed apparatus, between which coating steps driving steps are preferably performed. When performing a drying step it is not necessary to interrupt the fluidized bed process, though of course spraying must be halted during the drying step. The drying step, if performed, takes approximately 10 to 20 minutes. According to the present invention the active ingredient is preferably dispersed together with the excipients, in particular the microcrystalline cellulose and the binder, in a suitable solvent, preferably water, and the aqueous dispersion is then sprayed in a known manner on the neutral pellets. The stabilizing effect of the microcrystalline cellulose is particularly notable, if this type of manufacturing process is used. After performing an optional drying step, the separating layer is preferably applied in a similar manner, after which, preferably following a drying step, the enteric coating is then applied by spraying in a similar manner.

The present invention is described in greater detail with reference to the examples below.

COMPARATIVE EXAMPLE 1 a) Manufacture of Pellets Containing Active Ingredient by Suspension Layering 6.7 kg of Type 603 hydroxyproplymethylcellulose are dissolved in 50 l of de-mineralized water. In a second preparation 1.0 kg of $Na_2HPO_4$ (alkaline-reacting compound) is initially dissolved in 5 l of de-mineralized water. In this second solution 13.3 kg of omeprazole are dispersed with an Ultra-Turrax. Finally, 1.0 kg of polysorbate 80 is mixed with the dispersion containing the active ingredient. Both solutions/dispersions are slowly combined and carefully stirred. The entire mixture is then sprayed on 36.5 kg of neutral pellets in a conventional fluidized bed apparatus suitable for such purpose (e.g. Glatt-Wurster-type apparatus). Rate of spray and inlet air temperature are regulated to obtain a product temperature of about 35 to 40° C.

b Application of Separating Layer:

A separating layer is applied to the pellets containing the active ingredient from an aqueous solution. The solution is prepared by dissolving 3.5 kg of PEG 4000 and 17.3 kg of Type 603 hydroxypropylmethylcellulose in a total of 216 l of de-mineralized water. The solution is then also sprayed onto the pellets containing the active ingredient of step a) in the apparatus used in the previous step and at the same settings.

c Application of an Enteric Coating

Initially, 1.3 kg of glycerol monostearate is dispersed in 30 kg of de-mineralized water, heated to 65° C. and cooled. In an additional 70 kg of de-mineralized water 6.0 kg of PEG 6000 are dissolved and this solution is then combined with the glycerol monostearate dispersion. Once the mixture has completely cooled to room temperature, 133 kg of Eudragit L30D55 are added, and the entire dispersion is then slowly stirred. Optionally, the pH-value of the dispersion is adjusted using NaOH. The coating dispersion is then sprayed in a suitable coating device onto the pellets coated with the separating layer produced in step b).

COMPARATIVE EXAMPLE 2

Pellets containing omeprazole are produced in a similar manner to those in comparative example 1, in which however triethylcitrate is used instead of polyethlyenglycol as a plasticizer in the application of the enteric coating.

EXAMPLE 1

2.8 kg of omeprazole and 1.4 kg of microcrystalline cellulose of the type AVICEL-PH®-105 from FMC (mean particle size 20 μm, granular size distribution such that less than 0.1% of particles are 250 μm or larger in size and less than 1% of particles are 75 μm or larger in size) are dispersed by means of an Ultra-Turrax in 15.8 kg of de-mineralized water. 2.8 kg of hydroxypropylmethylcellulose are dissolved in a second preparation also in 15.8 kg of de-mineralized water. Both preparations are combined and lightly stirred, then applied using the apparatus and techniques described in comparative example 1 to 2.8 kg of neutral pellets.

The separating layer is applied as described in comparative example 1 using 1.6 kg microcrystalline cellulose of the type AVICEL-PH®-105 and 3.1 kg of HPMC in 35 kg of de-mineralized water.

Next, an enteric coating is applied as described in comparative example 1, using a dispersion of 17.5 kg of Eudragit L30D55, 1.3 kg PEG 6000, 200 g of glycerol monostearate and 14.9 kg of de-mineralized water. The coating is applied by spraying.

EXAMPLE 2

Pellets containing an active ingredient are manufactured in the manner prescribed in Example 1 with lansoprazole as the active ingredient. The excipients employed and quantities used are shown in the table below.

EXAMPLE 3

In the same manner as described in Example 1, pellets containing an active ingredient are manufactured using omeprazol. The excipients employed and quantities used are shown in the table below. The pellets were compressed into a "multiple unit dosage form" in accordance with conventional techniques.

EXAMPLE 4

The pellets of the comparative examples and of the examples were subjected to a conventional storage test under open conditions (40° C./75% relative humidity), and decomposition of the active ingredient after four weeks in storage was determined in accordance with known methods.

The following table summarizes the pellet components of comparative examples 1 and 2 and of examples 1, 2 and 3 and compares the results of the storage test.

| Amounts in mg/unit dosis | Comparative Example 1 | Comparative Example 2 | Example 1 | Example 2 | Example 3 |
|---|---|---|---|---|---|
| A) Layer with active ingredient | | | | | |
| Lansoprazole | | | | 15.0 | |
| Omeprazole | 20.0 | 20.0 | 20.0 | | 20 |
| HPMC | 10.0 | 10.0 | 20.0 | 15.0 | 20 |
| Microcrystalline cellulose | | | 10.0 | 7.5 | 10 |
| $Na_2HPO_4$ | 1.5 | 1.5 | | | |
| Polysorbate 80 | 1.5 | 1.5 | | | |
| Neutral pellets | 36.5 | 36.5 | 20.0 | 75.0 | 20 |
| B) Separating layer | | | | | |
| HPMC | 26.0 | 26.0 | 22.5 | 13.4 | 24 |
| PEG 6000 | 5.2 | 5.2 | | | |
| Microcrystalline cellulose | | | 11.3 | 6.7 | 12 |
| C) MSR Film | | | | | |
| Eudragit L | 60.0 | 60.0 | 38.0 | 30.6 | 38.75 |
| Eudragit NE | | | | | 11.25 |
| PEG 6000 | 9.0 | | 9.5 | 1.5 | 5.81 |
| Glycerol mono stearate | 2.0 | 2.0 | 1.1 | | 1.50 |
| Talcum | | | | 7.7 | |
| Triethylcitrate | | 9.0 | | | |
| Sodium hydroxide | pH-value-adjustment to pH 4 to 6.5 as required or per manufacturer specifications | | | | |
| Decomposition at 40/75, open storage | | | | | |
| After 4 weeks | 48.7% | 45.4% | 16.5% | 3.3% | 13.0% |

The results indicate that there is considerably less decomposition of the omeprazole in the pharmaceutical preparation according to the present invention as compared with pharmaceuticals in which omeprazole has been stabilized not by combining it with microcrystalline cellulose, but by adding a small amount of alkaline buffer compound capable of producing an alkaline pH-value. The amount of Eudragit was selected to ensure that the thickness of the enteric coating is comparable and it met the recommendations of the enteric polymer manufacturer. This was intended to eliminate effects caused by a variation in thickness of the enteric coating. To eliminate all possible doubt as to the stabilizing effect of the microcrystalline cellulose, a somewhat thicker layer, at the very least, was chosen for the enteric coatings in the comparative examples; thus the pellets of the comparative examples would more likely be expected to provide improved stabilization of the active ingredient.

EXAMPLE 5

The stability of the pellets according to Example 1 was compared with the stability of the commercial product ANTRA MUPS®. ANTRA MUPS® is a "multiple unit dosage form" with omeprazole as active ingredient, that is, pellets containing omeprazole compressed into tablet form.

Under the same conditions as described above, (open storage for 4 weeks at 40° C. and 75% relative humidity), decomposition of the active ingredient in the ANTRA MUPS® product after 4 weeks reached 25% as opposed to just 13% in the pharmaceutical preparation of example 3, which again shows the excellent stabilizing effect achievable according to the present invention through the combination of microcrystalline cellulose with a benzimidazole derivative of formula I.

The invention claimed is:

1. An oral pharmaceutical preparation in the form of pellets containing a benzimidazole compound of formula I

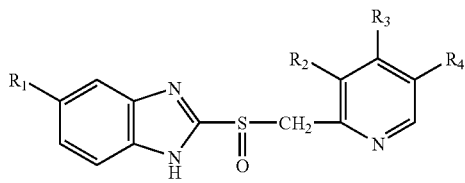

in which $R_1$ is hydrogen, methoxy or difluoromethoxy, $R_2$ is hydrogen, methyl or methoxy, $R_3$ is methoxy, 2,2,2-trifluoroethoxy or 3-methoxypropoxy and $R_4$ is hydrogen, methyl or methoxy, comprising
  (a) an inert core
  (b) to which is applied a layer containing an active ingredient which contains the benzimidazole compound of formula I
  (c) one or more optional separating layers and
  (d) an outer layer comprising an enteric coating,
  wherein the benzimidazole compound of formula I is mixed with a stabilizer comprising microcrystalline cellulose.

2. The pharmaceutical preparation according to claim 1, in which the benzimidazole compound of formula I is omeprazole, lansoprazole, rabeprazole or pantoprazole.

3. The pharmaceutical preparation according to claim 1, in which the microcrystalline cellulose is composed of particles size of 100 μm or less.

4. The pharmaceutical preparation according to claim 3, in which the microcrystalline cellulose is composed of particles having a mean particle size of 50 μm or less.

5. The pharmaceutical preparation according to claim 4, in which the microcrystalline cellulose is composed of particles having a particle size of about 20 μm.

6. The pharmaceutical preparation according to claim 3, in which the particle size distribution of the microcrystalline cellulose is such that less than 10% of the particles are 250 μm or greater in size and less than 50% of the particles are 75 μm or greater in size.

7. The pharmaceutical preparation according to claim 4, in which the particle size distribution of the microcrystalline cellulose is such that less than 2% of the particles are 250 μm or greater in size and less than 30% of the particles are 75 μm or greater in size.

8. The pharmaceutical preparation according to claim 5, in which the particle size distribution of the microcrystalline cellulose is such that less than 0.1% of the particles are 250 μm or greater in size and less than 1% of the particles are 75 μm or greater in size.

9. The pharmaceutical preparation according to claim 1, in which the microcrystalline cellulose has a bulk density of 0.30 g/cm³ or less.

10. The pharmaceutical preparation according to claim 9, in which the microcrystalline cellulose has a bulk density of 0.30 g/cm³ or less.

11. The pharmaceutical preparation according to claim 1, in which the layer with the active ingredient contains a binder which is hydroxypropylmethylcellulose or hydroxypropylcellulose.

12. The pharmaceutical preparation according to claim 1, in which the amount of microcrystalline cellulose is 25% to 150%, based on the weight of the amount of benzimidazole compound of formula I.

13. The pharmaceutical preparation according to claim 1, which has a separating layer containing microcrystalline cellulose and a binder.

14. The pharmaceutical preparation according to claim 13, in which the separating layer contains a binder which is hydroxypropylmethylcellulose or hydroxypropylcellulose.

15. The pharmaceutical preparation according to any one of claims 13 or 14, in which the separating layer contains microcrystalline cellulose in the amount of 25% to 100% by weight based on the amount of binder.

16. A method for manufacturing a pharmaceutical preparation according to claim 1, in which the benzimidazole compound of formula I is applied to an inert core to thereby form a layer with active ingredient, to which layer with active ingredient a separating layer is optionally applied, and an outer layer in the form of an enteric coating is applied.

17. The method according to claim 16, in which the layer containing the active ingredient is applied from an aqueous dispersion.

18. A method for improving the stability of a benzimidazole compound of formula I

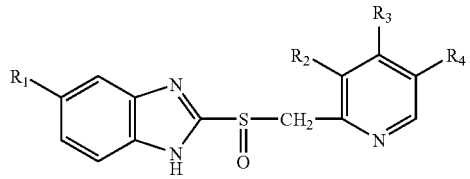

in which
  $R_1$ is hydrogen, methoxy or difluoromethoxy,
  $R_2$ is hydrogen, methyl or methoxy,
  $R_3$ is methoxy, 2,2,2-trifluoroethoxy or 3-methoxypropoxy and
  $R_4$ is hydrogen, methyl or methoxy, wherein said compound is mixed with a stabilizer comprising microcrystalline cellulose to form a pellet comprising an inert core, an active ingredient layer, one or more optional separating layers and an outer layer comprising an enteric coating.

19. The method of claim 18, wherein the benzimidazole compound of formula I is omeprazole, lansoprazole, rabeprazole or pantoprazole.

* * * * *